(12) United States Patent
Goshima et al.

(10) Patent No.: US 11,565,450 B2
(45) Date of Patent: Jan. 31, 2023

(54) INJECTION MOLDED ARTICLE

(71) Applicant: Otsuka Pharmaceutical Co., Ltd., Tokyo (JP)

(72) Inventors: Takehiko Goshima, Kunitachi (JP); Yoshifumi Imazu, Hachioji (JP); Kenta Fuji, Hachioji (JP)

(73) Assignee: OTSUKA PHARMACEUTICAL CO., LTD., Tokyo (JP)

( * ) Notice: Subject to any disclaimer, the term of this patent is extended or adjusted under 35 U.S.C. 154(b) by 346 days.

(21) Appl. No.: 16/765,316

(22) PCT Filed: Sep. 28, 2018

(86) PCT No.: PCT/JP2018/036216
§ 371 (c)(1),
(2) Date: May 19, 2020

(87) PCT Pub. No.: WO2019/116680
PCT Pub. Date: Jun. 20, 2019

(65) Prior Publication Data
US 2020/0353658 A1  Nov. 12, 2020

(30) Foreign Application Priority Data
Dec. 15, 2017  (JP) .............................. JP2017-240129

(51) Int. Cl.
*B29C 45/70* (2006.01)
*B29C 45/27* (2006.01)
(Continued)

(52) U.S. Cl.
CPC ........ *B29C 45/2708* (2013.01); *B01L 3/5027* (2013.01); *B29C 33/42* (2013.01); *G01N 33/5302* (2013.01)

(58) Field of Classification Search
CPC ... B29C 45/2708; B29C 33/42; B01L 3/5027; G01N 33/5302
(Continued)

(56) References Cited

U.S. PATENT DOCUMENTS

| 8,404,193 B2 | 3/2013 | Sekihara et al. |
| 2011/0135538 A1 | 6/2011 | Goshima et al. |
| 2011/0135539 A1 | 6/2011 | Sekihara et al. |

FOREIGN PATENT DOCUMENTS

| JP | H06-315955 A | 11/1994 |
| JP | 2003-139065 A | 5/2003 |

(Continued)

OTHER PUBLICATIONS

EPO, Extended European Search Report for the related European Application No. 18888242.7, dated Nov. 9, 2020.
(Continued)

*Primary Examiner* — Rebecca C Bryant
(74) *Attorney, Agent, or Firm* — Lucas & Mercanti, LLP

(57) ABSTRACT

An injection molded article is obtained by injection molding a molten resin into a mold. The injection molded article includes: a base as a thin plate-shaped member that is connected to a gate of the mold; and a plurality of protrusions each integrally molded on the base and having a thickness greater than a plate thickness of the base. The plurality of protrusions have holes each extending through the base, and the holes in the respective protrusions are connected through another component to form a flow channel. A processed region processed to have a surface roughness greater than a surface roughness of a mirror surface region including a region between the holes on the base is formed in a projected region where a region having a predetermined thickness value is projected on the base.

6 Claims, 6 Drawing Sheets

(51) Int. Cl.
*B29C 33/42* (2006.01)
*B01L 3/00* (2006.01)
*G01N 33/53* (2006.01)

(58) Field of Classification Search
USPC .............................. 324/500, 503, 76.11, 600
See application file for complete search history.

(56) References Cited

FOREIGN PATENT DOCUMENTS

| | | | |
|---|---|---|---|
| JP | 2005-163585 A | | 6/2005 |
| JP | 2005231239 A | * | 9/2005 |
| JP | 2012-098074 A | | 5/2012 |
| JP | 2013-180548 A | | 9/2013 |
| JP | 2016-145730 A | | 8/2016 |
| WO | 2010/016359 A1 | | 2/2010 |
| WO | 2010/016372 A1 | | 2/2010 |
| WO | 2013/114771 A1 | | 8/2013 |

OTHER PUBLICATIONS

PCT, International Search Report for the corresponding application No. PCT/JP2018/036216, dated Dec. 11, 2018, with English translation (4 pages).

PCT, International Preliminary Report on Patentability for the corresponding application No. PCT/JP2018/036216, dated Jun. 16, 2020, with English translation (4 pages).

* cited by examiner

FIG.9

| | COMPARATIVE EXAMPLE 1 | COMPARATIVE EXAMPLE 2 | COMPARATIVE EXAMPLE 3 | EXAMPLE 1 | EXAMPLE 2 | EXAMPLE 3 |
|---|---|---|---|---|---|---|
| 1. BASE PLATE THICKNESS | 1.3mm | 1.3mm | 1.3mm | 1.3mm | 1.3mm | 1.3mm |
| 2. THICKNESS OF THICKEST PORTION | 4.2mm | 4.2mm | 4.2mm | 4.2mm | 4.2mm | 4.2mm |
| 3. AREA OF SMALLEST CIRCLE CONTAINING PROJECTED REGION | $1.4\pi\ mm^2$ | $1.4\pi\ mm^2$ | $1.4\pi\ mm^2$ | $1.4\pi\ mm^2$ | $1.4\pi\ mm^2$ | $1.4\pi\ mm^2$ |
| 4. PERCENTAGE OF PROCESSED REGION | 71% | 71% | 36% | 71% | 71% | 50% |
| 5. AREA OF PROCESSED REGION | $1\pi\ mm^2$ | $1\pi\ mm^2$ | $0.5\pi\ mm^2$ | $1\pi\ mm^2$ | $1\pi\ mm^2$ | $0.7\pi\ mm^2$ |
| 6. SURFACE ROUGHNESS OF PROCESSED REGION (Ra) | Ra0.5 $\mu m$ | Ra3 $\mu m$ | Ra1 $\mu m$ | Ra1 $\mu m$ | Ra2 $\mu m$ | Ra1 $\mu m$ |
| EVALUATION | × | × | × | ○ | ○ | ○ |
| REASON | NO ANCHOR EFFECT | REMAINING IN MOLD | NO ANCHOR EFFECT | | | |
| CAUSE | LOW ROUGHNESS | HIGH ROUGHNESS | SMALL PROCESSED REGION | | | |

INJECTION MOLDED ARTICLE

CROSS REFERENCE TO RELATED APPLICATION

This Application is a 371 of PCT/JP2018/036216 filed on Sep. 28, 2018 which, in turn, claimed the priority of Japanese Patent Application No. 2017-240129 filed on Dec. 15, 2017, both are incorporated herein by reference.

TECHNICAL FIELD

The present invention relates to an injection molded article that has a plurality of protrusions, so-called bosses and ribs, with different inner diameters on its substrate, and that is formed by injection molding involving separating the plurality of protrusions from a mold.

BACKGROUND ART

There is known an injection molded article that has protrusions with different inner diameters on its substrate, and that is formed by injection molding involving separating the plurality of protrusions from a mold.

When injection molding a plastic product having a relatively thin base (plate thickness) part that is connected to a gate of a mold, and a protrusion (such as a boss and a rib) or an uneven thickness part, a sink mark is formed, for example, on the surface of a portion where the thickness of the product greatly varies. A sink mark is caused by the following reason. A molten thermoplastic shrinks while being cooled and solidified in a mold. In this process, a portion with a greater thickness than the neighboring portion is cooled more slowly, and therefore solidifies and shrinks after the neighboring portion solidifies. In particular, the core-side portion in the fixed mold defining the product visible portion of a plastic product is generally flat and more quickly cooled than the cavity-side portion in the movable mold having complicated structures such as a boss and a rib. Therefore, the core-side portion in the fixed mold is separated from the mold earlier than the cavity-side portion in the movable mold including the project invisible portion, and causes post-shrinkage, which is likely to result in a sink mark.

A sink mark is a recessed depression on the surface of a product. Sink marks not only reduce the visual quality of the product and lower the value, but also prevent uniform painting and impair the appearance. This may increase the repair cost.

To solve this problem, there is disclosed a technique that controls the location of sink marks such that sink marks are formed on the invisible surface. This is achieved by performing injection molding using a mold configured such that the mold surface on the product visible surface side that would cause sink marks has a higher adhesion force to resin than the mold surface on the invisible surface side (see, for example, PTL 1).

PRIOR ART DOCUMENT

Patent Document

Patent Document 1: JP H6-315955 A

SUMMARY OF THE INVENTION

Problems to be Solved by the Invention

The product visible surface of a component of a micro fluid chip is required to prevent leakage of liquid and achieve the accuracy in height of a flow channel for fluid when an optical component is joined thereto. This is because the flow channel is formed by joining the optical component thereto.

However, according to the technique disclosed in PTL 1, since roughening is applied to the entire region of the product visible surface where sink marks would be formed, roughening is applied even to the region requiring accuracy in specularity that affects the height of the flow channel and leakage of liquid. That is, according to the technique disclosed in PTL 1, there are variations in the surface properties of the product visible surface, which results in leakage of liquid and variations in the height of the flow channel.

An object of the present invention is to provide an injection molded article that can prevent leakage of liquid and achieve the required accuracy in height of a flow channel.

Means for Solving Problem

In order to achieve the above-described object, an invention recited in claim 1 is an injection molded article that is obtained by injection molding a molten resin into a mold, the injection molded article including:

a base as a thin plate-shaped member that is connected to a gate of the mold; and a plurality of protrusions each integrally molded on the base and having a thickness greater than a plate thickness of the base;

wherein the plurality of protrusions have holes each extending through the base, and the holes in the respective protrusions are connected through another component to form a flow channel;

wherein when a thickness value of a thickest portion of the protrusions is defined as 100%, a processed region processed to have a surface roughness greater than a surface roughness of a mirror surface region including a region between the holes on the base is formed in a projected region where a region having a thickness value of 95 to 100% is projected on the base; and wherein the injection molded article is obtained from the mold processed such that the mirror surface region and the projected region are located close to each other.

The invention recited in claim 2 is the injection molded article according to claim 1, wherein the thickness of the thickest portion is two or more times greater than the plate thickness of the base.

The invention recited in claim 3 is the injection molded article according to claim 1 or 2, wherein the surface roughness of the processed region is 1 to 2 μm in Ra.

The invention recited in claim 4 is the injection molded article according to any one of claims 1 to 3, wherein when an area of a smallest circle containing the projected region is defined as 100%, the injection molded article is obtained from the mold roughened to make a surface roughness greater than the surface roughness of the mirror surface region, in an area that is within the smallest circle and is 50 to 100% of an area of the smallest circle.

The invention recited in claim 5 is the injection molded article according to any one of claims 1 to 4, wherein a region where a surface accuracy of the mold is not achieved is formed in a region where a region of the thickest portion is projected on an invisible surface defining a surface other than the base.

The invention recited in claim 6 is the injection molded article according to any one of claims 1 to 5, wherein the mirror surface region is included in a region where a region having a thickness value of 70 to 95% is projected on the base.

Advantageous Effects of Invention

According to the present invention, it is possible to achieve the required accuracy in height of the flow channel.

BRIEF DESCRIPTION OF DRAWINGS

FIG. 9 illustrates examples and comparative examples of test chip substrates.

EMBODIMENTS FOR CARRYING OUT INVENTION

Hereinafter, embodiments of the present invention will be described with reference to the accompanying drawings.

Basic Configuration of Test Chip

Figure 1:
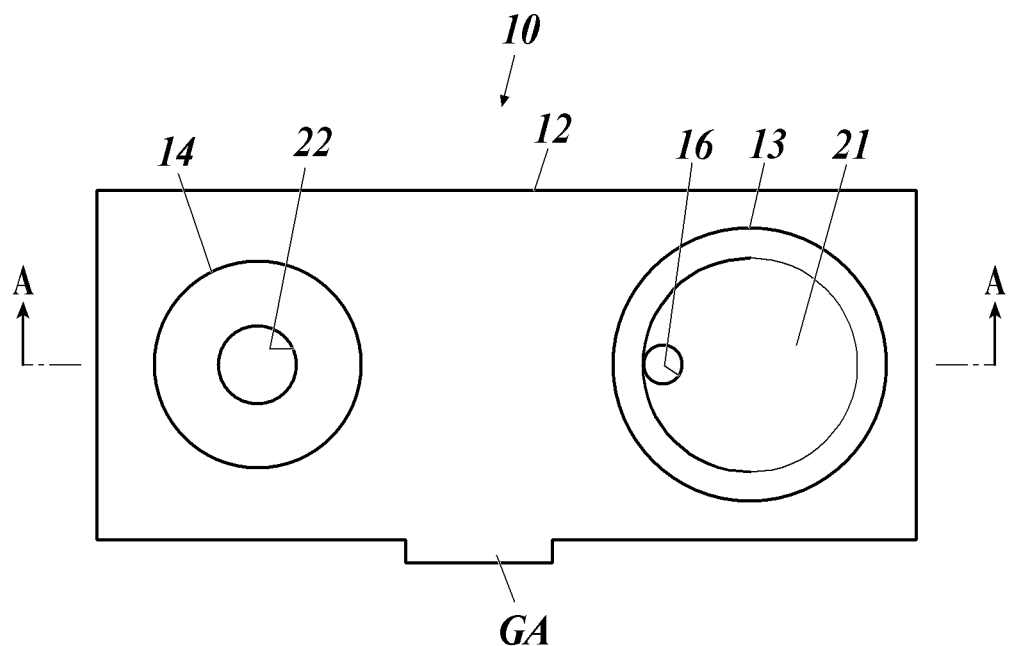
FIG. 1 is a plan view of a test chip called a micro fluid chip according to an embodiment.
Figure 2:
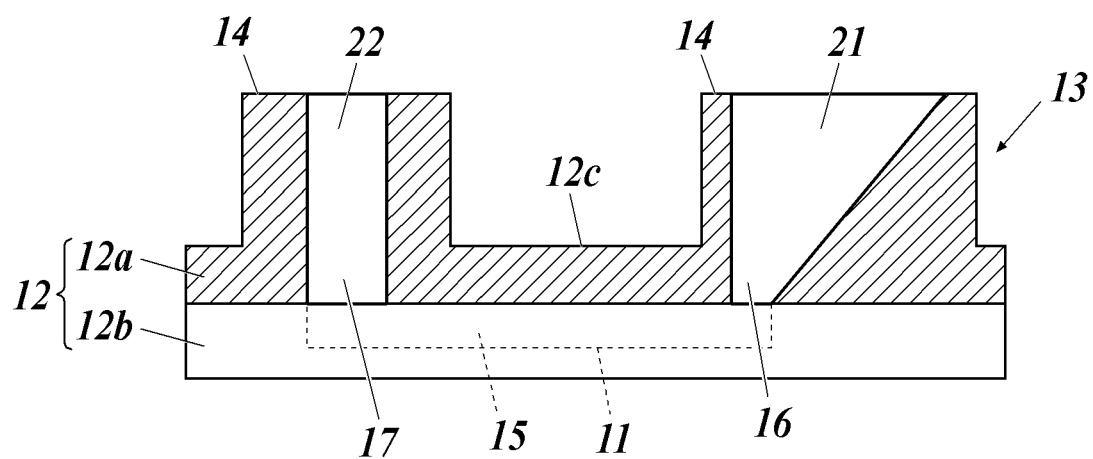
FIG. 2 is a cross-sectional view taken along the line A-A of FIG. 1.

A test chip 10 according to the present embodiment is a chip (micro fluid chip) used for test, analysis, and so on of a biological material based on an antigen-antibody reaction. As illustrated in FIGS. 1 and 2, the test chip 10 includes a test chip substrate 12, a first protrusion 13, and a second protrusion 14.

The test chip substrate 12 is made of a resin. The requirements for the resin are high formability (transformability and releasability), high transparency, and low self-fluorescence with respect to the ultraviolet ray and visible ray. The test chip substrate 12 has a flow channel 11 through which liquid or the like injected by a non-illustrated liquid feeder flows.

Test Chip Substrate

As illustrated in FIG. 2, the test chip substrate 12 includes a first substrate (base) 12a as a thin plate-shaped member, a flow channel seal (not illustrated), and a second substrate 12b (optical component such as a prism). The flow channel 11 is formed in a region defined by the first substrate 12a and the second substrate 12b attached together with a flow channel seal. The first substrate 12a and the second substrate 12b of the test chip substrate 12 are manufactured by a method such as injection molding, press molding, and machine processing. At least one of the first substrate 12a and the second substrate 12b may be microfabricated.

The first substrate 12a has a gate GA. The gate GA serves as an inlet when injecting a resin material into the mold. The gate GA has a bridging function for filling the cavity with the resin material injected through a sprue.

The test chip substrate 12 is formed by joining the first substrate 12a and the second substrate 12b. When the first substrate 12a and the second substrate 12b are joined, the flow channel 11 is formed therebetween. The substrates may be joined by a welding method that joins resin-made substrates by heating them using a heat plate, hot air, a heating roller, ultrasonic wave, vibration, laser, double-sided seal, or the like, a bonding method that joins resin-made substrates using adhesive or solution, a method that joins resin-made substrates utilizing their own adhesiveness, or a method that joins substrates by applying surface treatment such as plasma treatment to resin-made substrates. In this manner, the test chip 10 having the flow channel 11 therein is manufactured.

The flow channel 11 includes a reaction channel 15 extending in a predetermined direction (direction along an upper surface 12c of the test chip substrate 12 in FIG. 2) inside the test chip substrate 12, a communication channel 16 for communication between the reaction channel 15 and the first protrusion 13, and a communication channel 17 for communication between the reaction channel 15 and the second protrusion 14.

The following describes how the flow channel 11 is formed. A groove for a flow channel (a part corresponding to the reaction channel 15 in FIG. 2) is formed in the second substrate 12b. Then, the first substrate 12a serving as a cover is joined to the second substrate 12b having the flow channel groove, in a manner such that the flow channel groove faces inward. In this way, the flow channel 11 is formed. Alternatively, the flow channel 11 may be formed by joining the first substrate 12a and the second substrate 12b, in a manner such that a double-sided seal having the flow channel 11 is interposed therebetween.

The plate thickness of the second substrate 12b having the flow channel groove is preferably 0.2 mm to 5 mm, more preferably 0.5 mm to 2 mm. The plate thickness of the first substrate 12a serving as a lid (cover) for the flow channel groove is preferably 0.2 mm to 5 mm, more preferably 0.5 mm to 2 mm, taking into account the formability.

The test chip substrate 12 is made of a low-cost, disposable resin, specifically a thermoplastic resin. Preferred examples of thermoplastic resins are polycarbonate, polymethylmethacrylate, polystyrene, polyacrylonitrile, polyvinyl chloride, polyethylene terephthalate, nylon 6, nylon 66, polyvinyl acetate, polyvinylidene chloride, polypropylene, polypropylene, polyisoprene, polyethylene, polydimethylsiloxane, and cyclic polyolefin. Particularly preferred examples are polymethylmethacrylate and cyclic polyolefin.

Protrusions

The first protrusion 13 is integrally formed on the upper surface of the test chip substrate 12 (first substrate 12a). The first protrusion 13 has an inner diameter portion 21, and serves as a reagent mixer and a reagent reactor for mixing and reacting a reagent in the inner diameter portion 21. Techniques for mixing and reacting a reagent are well known in the art, and will not be described herein. The inner diameter portion 21 communicates with the communication channel 16 of the flow channel 11.

The second protrusion 14 is integrally formed on the upper surface of the test chip substrate 12, but in a region different from the region where the first protrusion 13 is formed. The second protrusion 14 has an inner diameter portion 22. The inner diameter portion 22 communicates with the communication channel 17 of the flow channel 11.

The first protrusion 13 and the second protrusion 14 respectively have holes 13a and 14a each extending through the first substrate 12a. The holes 13a and 14a in the respective protrusions (first protrusion 13 and second protrusion 14) are connected through another component (second substrate 12b) to form the flow channel 11.

Each of the first protrusion 13 and the second protrusion 14 is formed to have a thickness greater than a plate thickness of the first substrate 12a. In the present embodiment, the thickness of the thickest portion of the protrusions is two or more times greater than the plate thickness of the first substrate 12a.

Figure 3:
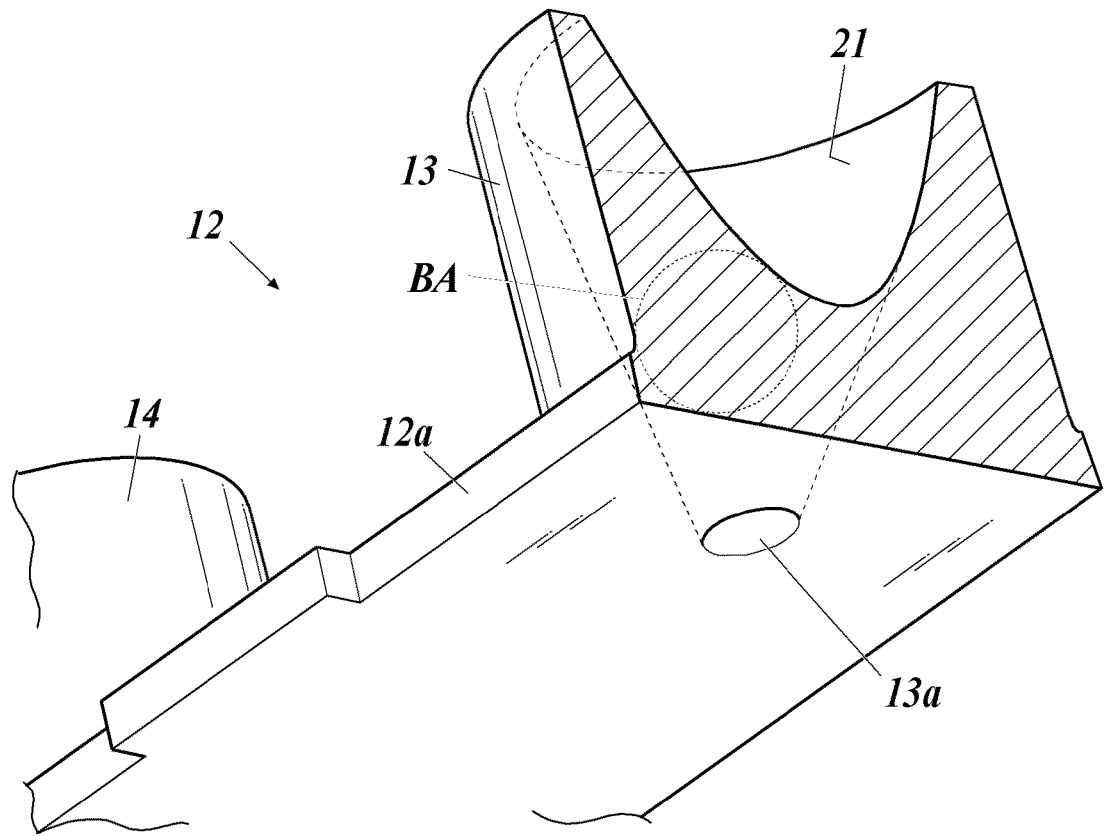
FIG. 3 is a cross-sectional view of a main part illustrating an example in which a sphere is located inside a first protrusion so as to be tangent to the wall surface.

As illustrated in FIG. 3, the thickest portion of the protrusions is the center of a sphere BA that is the largest imaginary sphere located inside the injection molded article (inside the first protrusion 13 in the present embodiment) and tangent to the wall surface thereof. The thickest portion of the protrusion can be calculated with, for example, the maximum ball algorithm used in 3D shape analysis software.

Figure 4:
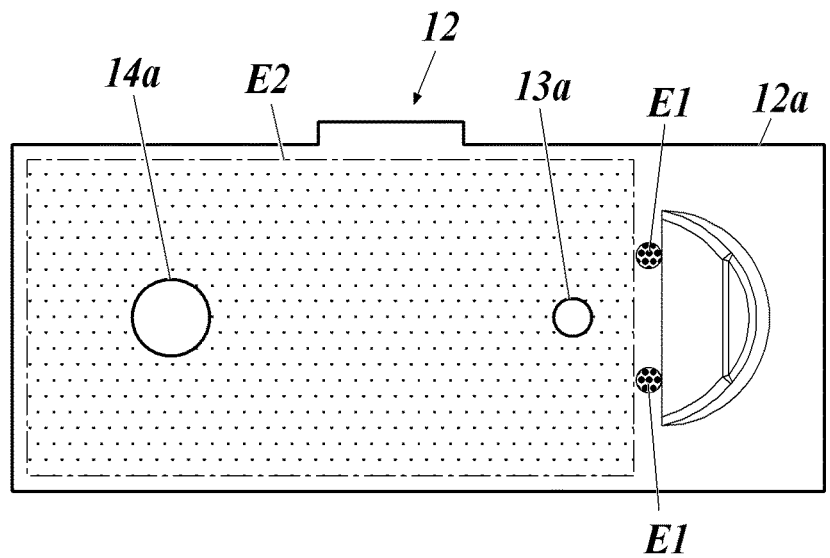
FIG. 4 is a bottom view illustrating an example of a projected region and a mirror surface region of a first substrate.

As illustrated in FIG. 4, when a thickness value of the thickest portion of the protrusions (in the present embodiment, the thickest portion of the first protrusion 13) is defined as 100%, a processed region processed to have a surface roughness greater (by several nanometers to several tens of nanometers in Ra) than the surface roughness of a mirror surface region E2 including a region between the holes 13a and 14a on the first substrate 12a is formed in a projected region E1 (that is, a region where a perpendicular line is drawn from a region having a thickness value of 95 to 100% to the first substrate 12a) where a region having a thickness value of 95 to 100% is projected on the first substrate 12a. In the present embodiment, the surface roughness of the processed region is 1 to 2 μm in Ra (arithmetic average roughness).

The injection molded article of the present invention is the test chip 10 excluding the second substrate 12b that is an optical component.

Figure 5:
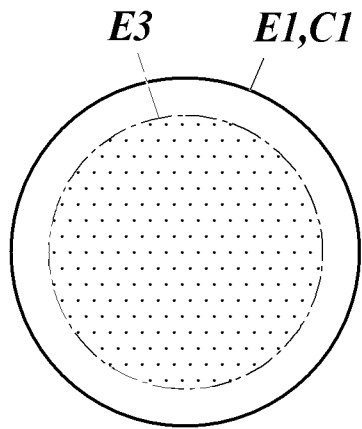
FIG. 5 is an enlarged view of a main part illustrating an example of a projected region and a processed region of a first substrate.

As illustrated in FIG. 5, when the area of a smallest circle C1 containing the projected region E1 is defined as 100%, the injection molded article of the present invention is obtained from a mold roughened (for example, sandblasted) to make the surface roughness greater than the surface roughness of the mirror surface region E2, in an area of a circle (=processed region E3) that is within the smallest circle C1 and is 50 to 100% of the area of the smallest circle C1. In the present embodiment, for purposes of explanation, the projected region E1 is circular, and the projected region E1 and the smallest circle C1 exactly coincide. However, the present invention is not limited thereto. That is, the projected region E1 is not always circular, and hence the projected region E1 and the smallest circle C1 do not always coincide. Also, the processed region E3 is not always circular, and may have any shape as long as its area is in the range of 50 to 100% of the area of the smallest circle C1.

Figure 6:
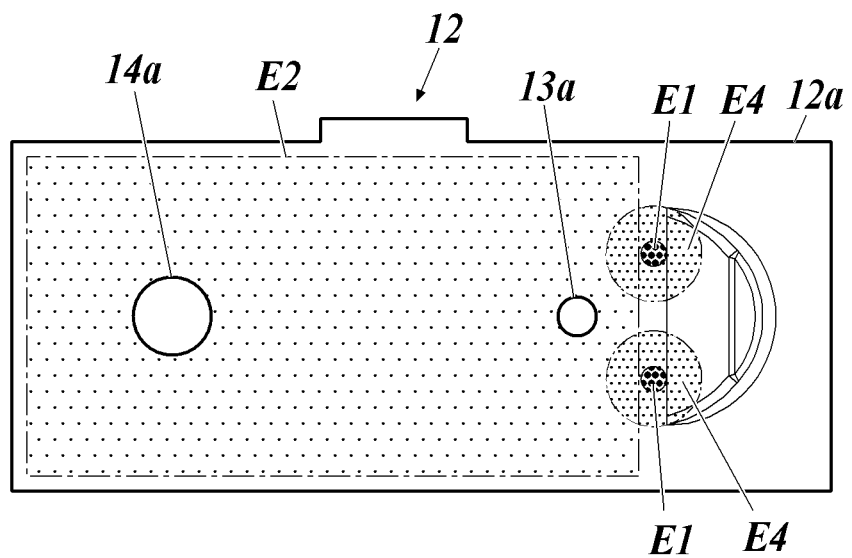
FIG. 6 is a bottom view illustrating an example in which the mirror surface region is included in a region where a region having a thickness value of 70 to 95% is projected on the first substrate.

The injection molded article of the present invention is obtained by injection molding a molten resin into a mold that is processed such that the mirror surface region E2 and the projected region E1 are located close to each other. Specifically, as illustrated in FIG. 6, the mirror surface region E2 is included in a region E4 (a region adjacent to the projected region E1) where a region having a thickness value of 70 to 95% is projected on the first substrate 12a. That is, the mirror surface region E2 is located close to the projected region E1 where sink marks are likely to be formed. Although it is necessary to prevent formation of sink marks, roughening cannot be applied to the mirror surface region E2 because flatness and specularity are required there. Accordingly, in the present embodiment, roughening is applied to the region close to the mirror surface region E2. That is, according to the present invention, even when the region (projected region E1) where sink marks are likely to be formed and the region (mirror surface region E2) requiring flatness and specularity are close to each other, formation of sink marks on the visible surface of the first substrate 12a is prevented.

Injection Molding

Figure 7:
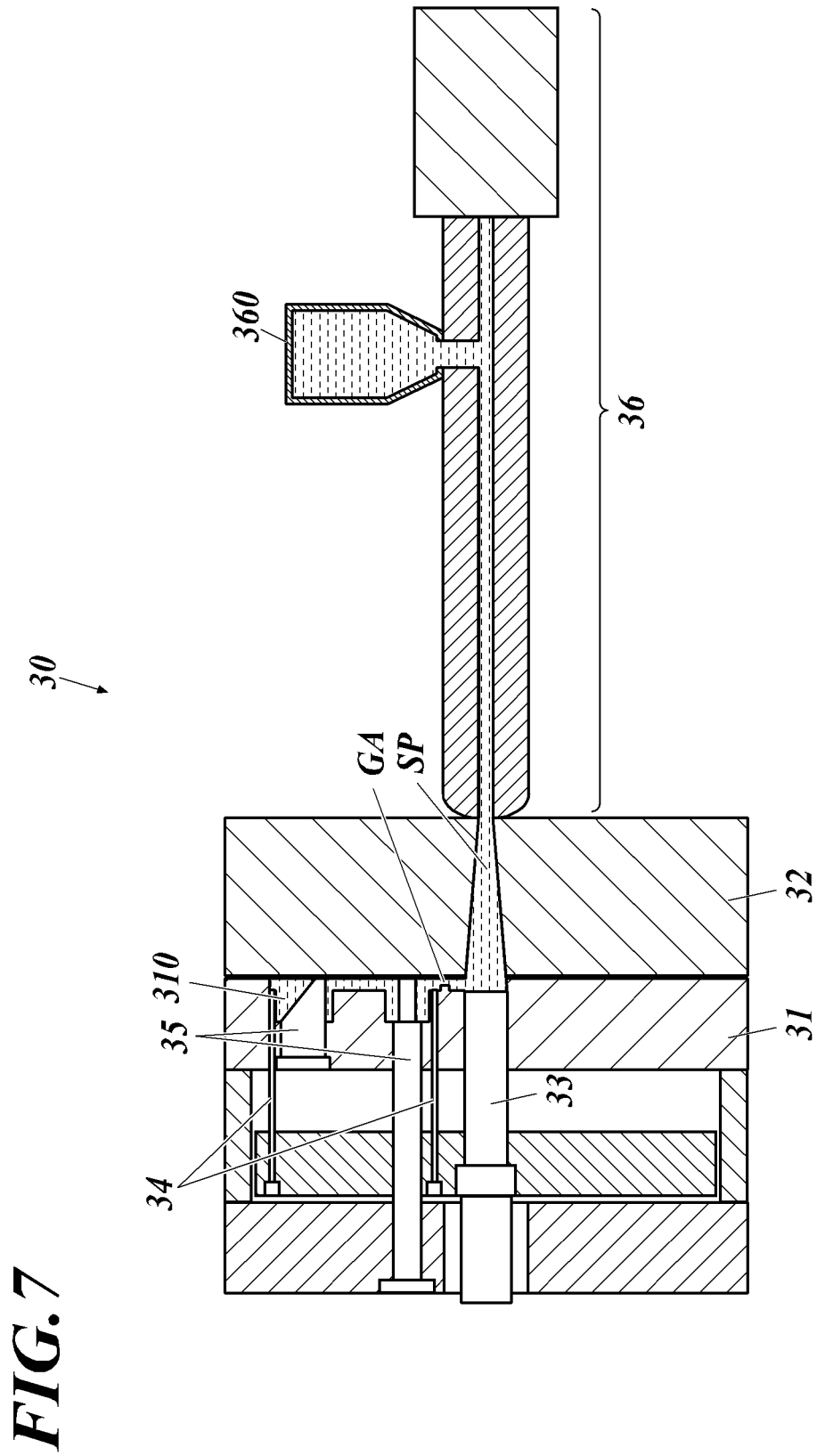
FIG. 7 is a schematic diagram illustrating a mold clamping step.
Figure 8:
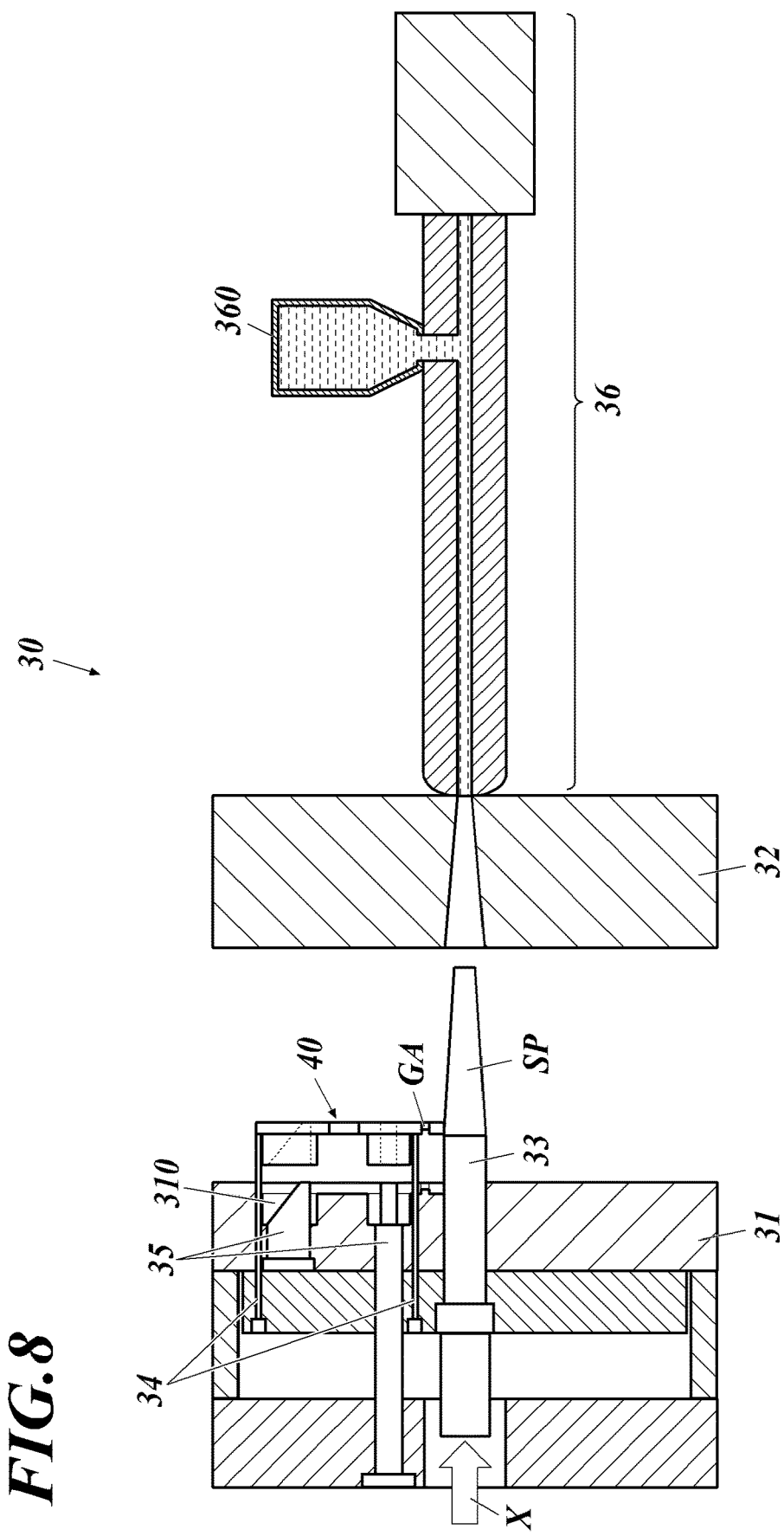
FIG. 8 is a schematic diagram illustrating an ejection step.

The test chip 10 is produced through a predetermined process by using an injection molding machine (injection mold 30). Hereafter, the injection molding process using the injection mold 30 will be described with reference to FIGS. 7 and 8. FIG. 7 is a schematic diagram illustrating a so-called "mold clamping step" for forming a cavity by clamping two molds (movable mold 31 and fixed mold 32). FIG. 8 is a schematic diagram illustrating a so-called "ejection step" for removing an injection molded article 40 from the injection mold 30.

As illustrated in FIG. 7, the injection mold 30 includes the movable mold 31 with a recess (cavity) 310 in the shape of the injection molded article 40, the fixed mold 32 against which the movable mold 31 is pressed so as to close the recess 310, an ejector pin 33 that pushes the injection molded article 40 outward (in the direction of the arrow X in FIG. 8), an ejector member 34, core pins 35 each defining the internal shape of a protrusion, and a cylinder unit 36 that supplies a resin material (not illustrated) as the material of the injection molded article 40 to the cavity.

The injection molding process includes a mold clamping step, an injection step, a pressure holding step, a cooling step, a mold opening step, and an ejection step. Injection molding is performed in this order. As illustrated in FIG. 7, in the mold clamping step, the movable mold 31 and the fixed mold 32 are clamped together to close the recess 310 formed in the movable mold 31, thereby forming a cavity. Then, a resin material (molten resin) is injected from a resin material supply furnace 360 to fill the cavity therewith (injection step). The resin material flows through a sprue SP (unwanted portion of the injection molded article 40) and the gate GA, and is filled in the cavity. When filled in the cavity of the mold, the resin material is cooled and shrinks in the mold. Since the shrinkage causes a change in the volume, this shrinkage action results in a dimensional change of a molded article, a shape transfer failure, and the like. To prevent these issues, the volume of resin reduced due to the shrinkage is compensated for by applying a holding pressure on the molding machine side (pressure holding step). Then, the resin material is cooled in the mold until its temperature decreases to a level at which it can be extracted from the mold (cooling step).

When the resin material is sufficiently cooled after a lapse of a predetermined time, the movable mold 31 is separated from the fixed mold 32 (mold opening step) as illustrated in FIG. 8. In this step, the molded article comes with the movable mold 31. Then, by moving the ejector pin 33 and the ejector member 34 outward, the injection molded article 40 is demolded (ejection step). The second substrate 12b is joined to the injection molded article 40 to obtain a test chip 10.

In the present embodiment, since the predetermined region (the region corresponding to the processed region of the first substrate 12a) of the surface of the fixed mold 32 is roughened (sandblasted), resin is not easily separated from the fixed mold 32 during cooling and shrinkage. This prevents formation of sink marks on the visible surface of the injection molded article 40 (first substrate 12a).

EXAMPLES

In the following, Examples 1 to 3 and Comparative Examples 1 to 3 of the test chip substrate 12 (first substrate 12a) according to the present invention will be described with reference to FIG. 9.

Comparative Example 1

A test chip substrate 12 of Comparative Example 1 is configured such that the plate thickness of a first substrate 12a (base plate thickness) is 1.3 mm, and the thickness value of the thickest portion of the first substrate 12a is 4.2 mm. The area of a smallest circle C1 containing a projected region E1 is $1.4\pi$ mm$^2$; the area of a processed region E3 is $1\pi$ mm$^2$; and the ratio (percentage) of the area of a processed region E3 to the area of the smallest circle C1 is 71%. The surface roughness of the processed region E3 is 0.5 µm in Ra.

Comparative Example 2

A test chip substrate 12 of Comparative Example 2 is configured such that the plate thickness of a first substrate 12a (base plate thickness) is 1.3 mm, and the thickness value of the thickest portion of the first substrate 12a is 4.2 mm. The area of a smallest circle C1 containing a projected region E1 is $1.4\pi$ mm$^2$; the area of a processed region E3 is $1\pi$ mm$^2$; and the ratio (percentage) of the area of a processed region E3 to the area of the smallest circle C1 is 71%. The surface roughness of the processed region E3 is 3 µm in Ra.

Comparative Example 3

A test chip substrate 12 of Comparative Example 3 is configured such that the plate thickness of a first substrate 12a (base plate thickness) is 1.3 mm, and the thickness value of the thickest portion of the first substrate 12a is 4.2 mm. The area of a smallest circle C1 containing a projected region E1 is $1.4\pi$ mm$^2$; the area of a processed region E3 is $0.5\pi$ mm$^2$; and the ratio (percentage) of the area of a processed region E3 to the area of the smallest circle C1 is 36%. The surface roughness of the processed region E3 is 1 µm in Ra.

Example 1

A test chip substrate 12 of Example 1 is configured such that the plate thickness of a first substrate 12a (base plate thickness) is 1.3 mm, and the thickness value of the thickest portion of the first substrate 12a is 4.2 mm. The area of a smallest circle C1 containing a projected region E1 is $1.4\pi$ mm$^2$; the area of a processed region E3 is $1\pi$ mm$^2$; and the ratio (percentage) of the area of a processed region E3 to the area of the smallest circle C1 is 71%. The surface roughness of the processed region E3 is 1 µm in Ra.

Example 2

A test chip substrate 12 of Example 2 is configured such that the plate thickness of a first substrate 12a (base plate thickness) is 1.3 mm, and the thickness value of the thickest portion of the first substrate 12a is 4.2 mm. The area of a smallest circle C1 containing a projected region E1 is $1.4\pi$ mm$^2$; the area of a processed region E3 is $1\pi$ mm$^2$; and the ratio (percentage) of the area of a processed region E3 to the area of the smallest circle C1 is 71%. The surface roughness of the processed region E3 is 2 µm in Ra.

Example 3

A test chip substrate 12 of Example 3 is configured such that the plate thickness of a first substrate 12a (base plate thickness) is 1.3 mm, and the thickness value of the thickest portion of the first substrate 12a is 4.2 mm. The area of a smallest circle C1 containing a projected region E1 is $1.4\pi$ mm$^2$; the area of a processed region E3 is $0.7\pi$ mm$^2$; and the ratio (percentage) of the area of a processed region E3 to the area of the smallest circle C1 is 50%. The surface roughness of the processed region E3 is 1 µm in Ra.

Evaluation

In the case of the test chip substrate 12 of Comparative Example 1 configured such that the surface roughness of the processed region E3 is 0.5 µm in Ra, since the roughness was too low, the resin did not properly stick to the mold. Accordingly, satisfactory results were not obtained.

In the case of the test chip substrate 12 of Comparative Example 2 configured such that the surface roughness of the processed region E3 is 3 µm in Ra, since the roughness was too high, the resin remained in the mold. Accordingly, satisfactory results were not obtained.

In the case of the test chip substrate 12 of Comparative Example 3 configured such that the ratio (percentage) of the area of the processed region E3 to the area of the smallest circle C1 is 36%, since the area was too small, the resin did not properly stick to the mold. Accordingly, satisfactory results were not obtained.

Meanwhile, in the case of the test chip substrates 12 of Examples 1 to 3, satisfactory results were obtained.

It was found from the above that when the test chip substrate 12 is configured such that the surface roughness of the processed region E3 is 1 to 2 µm in Ra, satisfactory results are obtained. It was also found that when the test chip substrate 12 is configured such that the ratio (percentage) of the area of the processed region E3 to the area of the smallest circle C1 is 50 to 100%, satisfactory results are obtained.

With any of the configurations of Examples 1 to 3, it is possible to prevent formation of sink marks on the visible surface of the first substrate 12a.

Meanwhile, a region where the surface accuracy of the mold is not achieved is formed in a region where the region of the thickest portion is projected on the invisible surface (for example, the side wall of the protrusion) defining the surface other than the visible surface. The region where the surface accuracy of the mold is not achieved is a region where the shape of the mold is not accurately transferred, and is a region where a so-called sink mark is formed. That is, in the present embodiment, formation of sink marks on the visible surface of the first substrate 12a is prevented by guiding sink marks to the invisible surface.

Advantageous Effects

As described above, the injection molded article according to the present embodiment includes: a base (first substrate 12a) as a thin plate-shaped member that is connected to the gate GA of a mold (injection mold 30); and a plurality of protrusions (first protrusion 13 and second protrusion 14) each integrally molded on the base and having a thickness greater than a plate thickness of the base. The plurality of protrusions have holes 13a and 14a each extending through the base, and the holes 13a and 14a in the respective protrusions are connected through another component to form a flow channel. When the thickness value of the thickest portion of the protrusions is defined as 100%, the processed region E3 processed to have a surface roughness greater than the surface roughness of the mirror surface region E2 including a region between the holes 13a and 14a on the base is formed in the projected region E1 where a region having a thickness value of 95 to 100% is projected on the base. The injection molded article is obtained from the mold processed such that the mirror surface region E2 and the projected region E1 are located close to each other.

Accordingly, according to the injection molded article of the present embodiment, the region of the product visible surface in which sink marks are likely to be formed is processed such that resin is not easily separated, so that formation of sink marks on the product visible surface is prevented. Accordingly, the surface properties of the product visible surface are sufficiently secured. Therefore, it is possible to prevent leakage of liquid, and achieve the required accuracy in height of the flow channel.

According to the injection molded article of the present embodiment, the thickness of the thickest portion is two or more times greater than the plate thickness of the base.

Accordingly, according to the injection molded article of the present embodiment, even when the molded artic has a large thickness, formation of sink marks on the visible surface is prevented. Therefore, it is possible to prevent leakage of liquid, and achieve the required accuracy in height of the flow channel.

According to the injection molded article of the present embodiment, the surface roughness of the processed region E3 is 1-2 μm in Ra.

Accordingly, according to the injection molded article of the present embodiment, the resin on the product visible surface side adheres sufficiently well, so that formation of sink marks on the product visible surface is more reliably prevented.

According to the injection molded article of the present embodiment, when the area of the smallest circle C1 containing the projected region E1 is defined as 100%, the injection molded article is obtained from a mold roughened to make the surface roughness greater than the surface roughness of the mirror surface region E2, in an area that is within the smallest circle C1 and that is 50 to 100% of the area of the smallest circle C1.

Accordingly, according to the injection molded article of the present embodiment, the resin on the product visible surface side adheres sufficiently well, so that formation of sink marks on the product visible surface is more reliably prevented.

According to the injection molded article of the present embodiment, a region where a surface accuracy of the mold is not achieved is formed in a region where a region of the thickest portion is projected on an invisible surface defining a surface other than the base.

Accordingly, according to the injection molded article of the present embodiment, sink marks are guided to the invisible surface, so that formation of sink marks on the product visible surface is prevented.

According to the injection molded article of the present embodiment, the mirror surface region E2 is included in a region where a region having a thickness value of 70 to 95% is projected on the base.

Accordingly, according to the injection molded article of the present embodiment, even when the region (projected region E1) where sink marks are likely to be formed and the region (mirror surface region E2) requiring flatness and specularity are close to each other, formation of sink marks on the visible surface is prevented. Therefore, it is possible to prevent leakage of liquid, and achieve the required accuracy in height of the flow channel.

Although the present invention has been described in conjunction with the specific embodiment, the present invention is not limited to the above embodiment, and changes and modifications may be made without departing from the scope of the present invention.

Modifications

For example, in the above embodiment, the thickness of the thickest portion of the protrusions is two or more times greater than the plate thickness of the first substrate 12a. However, the present invention is not limited thereto. That is, the thickness of the thickest portion of the protrusions only needs to be greater than the plate thickness of the first substrate 12a. The thickness of the thickest portion of the protrusions may be less than twice the thickness of the first substrate 12a.

In the above embodiment, surface roughening is performed by sandblasting. However, the present invention is not limited thereto. For example, surface roughening is performed by rubbing with sand paper or etching, in place of sandblasting. Alternatively, fine indentations may be formed on the surface by using a processing machine capable of high precision processing so as to have a desired surface roughness (Ra).

Other changes and modifications may also be made to the configuration and operation of the devices included in the test chip without departing from the scope of the present invention.

INDUSTRIAL APPLICABILITY

The present invention is applicable to injection molded articles.

REFERENCE SIGNS LIST 10 test chip
11 flow path
12 test chip substrate
12a first substrate (base)
12b second substrate
13 first protrusion (protrusion)
14 second protrusion (protrusion)
13a, 14a hole
15 reaction channel
16, 17 communication channel
21, 22 inner diameter portion
30 injection mold
31 movable mold
310 recess
32 fixed mold
33 ejector pin
34 ejector member
35 core pin
36 cylinder unit
360 resin material supply furnace
40 injection molded article
GA gate
BA sphere
E1 projected region
E2 mirror surface region
E3 processed region
C1 smallest circle

The invention claimed is:

1. An injection molded article that is obtained by injection molding a molten resin into a mold, the injection molded article comprising:
a base, the base being a thin plate-shaped member that is connected to a gate of the mold; and
a plurality of protrusions each integrally molded on the base and having a thickness greater than a plate thickness of the base;
wherein the plurality of protrusions have holes each extending through the base;
wherein a projected region of the base is processed to have a surface roughness greater than a surface roughness of a mirror surface region surrounding the holes on the base, and the projected region is where a region of the protrusions having a thickness value of 95 to 100% is projected on the base when a thickness value of a thickest portion of the protrusions is defined as 100%; and wherein the injection molded article is obtained from the mold processed such that the mirror surface region and the projected region are located close to each other.

2. The injection molded article according to claim 1, wherein the thickness of the thickest portion is two or more times greater than the plate thickness of the base.

3. The injection molded article according to claim 1, wherein the surface roughness of the processed region is 1 to 2 μm in Ra.

4. The injection molded article according to claim 1, wherein when a first area of a smallest circle containing the projected region is defined as 100%, the injection molded article is obtained from the mold having a roughened region to make a surface roughness of a second area greater than the surface roughness of the mirror surface region, and the second area is within the smallest circle and is 50 to 100% of the first area of the smallest circle.

5. The injection molded article according to claim 1, wherein a sink mark is formed in a region where the thickest portion of the protrusions is projected on an invisible surface of the injection molded article other than a surface of the base.

6. The injection molded article according to claim 1, wherein the mirror surface region overlaps with a region where a region having a thickness value of 70 to 95% is projected on the base.

* * * * *